United States Patent
Nagano et al.

(10) Patent No.: US 8,425,465 B2
(45) Date of Patent: Apr. 23, 2013

(54) DRIVE DEVICE FOR LINEAR BODY

(75) Inventors: Yoshitaka Nagano, Iwata (JP); Yukihiro Nishio, Iwata (JP)

(73) Assignee: NTN Corporation, Osaka (JP)

( * ) Notice: Subject to any disclaimer, the term of this patent is extended or adjusted under 35 U.S.C. 154(b) by 0 days.

(21) Appl. No.: 12/934,203

(22) PCT Filed: Mar. 6, 2009

(86) PCT No.: PCT/JP2009/054275
§ 371 (c)(1),
(2), (4) Date: Sep. 23, 2010

(87) PCT Pub. No.: WO2009/119283
PCT Pub. Date: Oct. 1, 2009

(65) Prior Publication Data
US 2011/0046553 A1 Feb. 24, 2011

(30) Foreign Application Priority Data

Mar. 25, 2008 (JP) ................................. 2008-078050

(51) Int. Cl.
*A61M 5/20* (2006.01)
(52) U.S. Cl.
USPC ........................................................ 604/156
(58) Field of Classification Search .................. 604/156, 604/159, 528, 164.13, 164.01, 164.07, 510, 604/95.01; 600/114; 606/108
See application file for complete search history.

(56) References Cited

U.S. PATENT DOCUMENTS

| 5,779,623 | A | 7/1998 | Bonnell |
| 6,290,675 | B1 | 9/2001 | Vujanic et al. |
| 6,358,199 | B1 | 3/2002 | Pauker et al. |
| 2006/0041245 | A1 | 2/2006 | Ferry et al. |
| 2008/0045892 | A1 | 2/2008 | Ferry et al. |
| 2010/0057099 | A1* | 3/2010 | Fujimoto et al. ............. 606/130 |

FOREIGN PATENT DOCUMENTS

| JP | 3-92126 | 4/1991 |
| JP | 2000-42116 | 2/2000 |
| JP | 2001-157662 | 6/2001 |
| WO | WO 93/20876 A1 | 10/1993 |

OTHER PUBLICATIONS

Extended European Search Report, issued in European Patent Application No. 09 723 878.6, dated Nov. 4, 2011.

* cited by examiner

*Primary Examiner* — Laura A Bouchelle
*Assistant Examiner* — Brooke Matney
(74) *Attorney, Agent, or Firm* — McDermott Will & Emery LLP

(57) ABSTRACT

There is provided a drive device for a linear body, that allows a treatment to be immediately, manually resumed when an emergency arises. A drive device for a linear body includes a securing portion capable of securing a Y connector having a through hole, and an actuator including a driving roller and a driven roller moving the linear body that is inserted in the through hole of the Y connector in the longitudinal direction of the linear body. The drive device allows the linear body and the Y connector to be integrally, manually attached to and detached from the securing portion.

6 Claims, 4 Drawing Sheets

DRIVE DEVICE FOR LINEAR BODY

RELATED APPLICATIONS

This application is the U.S. National Phase under 35 U.S.C. §371 of International Application No. PCT/JP2009/054275, filed on Mar. 6, 2009, which in turn claims the benefit of Japanese Application No. 2008-078050, filed on Mar. 25, 2008, the disclosures of which Applications are incorporated by reference herein.

TECHNICAL FIELD

The present invention relates generally to drive devices for linear bodies and particularly to drive devices for catheters and other similar linear bodies for medical use.

BACKGROUND ART

Recently, less invasive surgeries such as treatments using catheters have been performed. FIG. 6 schematically shows a medical instrument used in a surgical treatment employing coil embolization for a treatment to prevent rupture of a cerebral aneurysm, a cause of subarachnoid hemorrhage.

FIG. 6 shows a medical instrument 100. In this instrument, a coil 101 formed of platinum is used for embolizing an aneurysm 133. Coil 101 is connected to a tip of a delivery wire 104. Delivery wire 104 is inserted in a Y connector 121, and a catheter 102 is inserted in a Y connector 111. Delivery wire 104 is manipulated by a doctor at a holding portion 106 located in a vicinity of an entrance of Y connector 121. Catheter 102 is manipulated by the doctor at a holding portion 105 located in a vicinity of an entrance of Y connector 111.

Y connector 111, 121 has three connection ports. One is a port for connecting a catheter. Another is a port for receiving a catheter, a delivery wire or a similar linear body. The other is ports 112, 122 for introducing physiological saline, agents and the like.

A catheter 103 is inserted in a blood vessel 132 of a human body 131 and has a tip having reached a vicinity of aneurysm 133. Catheter 102 is inserted in catheter 103, and delivered from a tip of catheter 103 into aneurysm 133. Catheter 102 reaches an interior of aneurysm 133 and coil 101 is pushed out from the catheter, and thus thin and soft coil 101 embolizes aneurysm 133. Aneurysm 133 is thus prevented from rupture.

Such a catheter treatment requires delicate control in manipulating a catheter, a delivery wire and the like. Accordingly, it requires a skilled operator. Accordingly, to improve the operability of the catheter, delivery wire and the like, some drive devices have been proposed (see Japanese Patent Laying-open No. 2000-42116 (patent document 1) and Japanese Patent Laying-open No. 2001-157662 (patent document 2), for example).

Patent Document 1: Japanese Patent Laying-open No. 2000-42116
Patent Document 2: Japanese Patent Laying-open No. 2001-157662

DISCLOSURE OF THE INVENTION

Problems to be Solved by the Invention

These documents describe drive devices causing a roller, a spherical body or the like to rotate by a motor or the like to operate a catheter or a similar linear body. However, if a power failure or some other emergency arises and the roller, spherical body or the like cannot be operated, the linear body pinched by the roller, spherical body or the like must be pulled out manually to resume the treatment. In other words, there has not been means for pulling out the linear body that has been inserted in a blood vessel, aneurysm or the like from the drive device without changing the position of the linear body.

The present invention has been made to overcome the above problem, and it mainly contemplates a drive device for a linear body, that allows a treatment to be immediately, manually resumed when a power failure or similar emergency arises.

Means for Solving the Problems

The present invention provides a drive device for a linear body, including: a securing portion capable of securing a member to be secured having a through hole; and an actuator moving a linear body that is inserted in the through hole of the member to be secured in a longitudinal direction of the linear body. The drive device allows the linear body and the member to be secured to be integrally, manually attached to and detached from the securing portion.

Preferably, the drive device for a linear body includes a housing having a lid member opened/closed as desired. By closing the lid member, the linear body and the member to be secured are integrally attached to the securing portion, and by opening the lid member, the linear body and the member to be secured are integrally removable from the securing portion.

Preferably, the drive device for a linear body further includes an elastic body attached to the lid member. The lid member has a lever operated to open/close the lid member. When the lid member is closed, the elastic body presses the lid member with elastic force, which presses and thus fixes the lever. The lever is elastically deformed to open the lid member.

Preferably, the actuator includes a torque generator, a driving roller performing rotational motion by torque generated by the torque generator, and a driven roller performing rotational motion as the driving roller rotates. The driving roller and the driven roller have a rotation surface and a rotation surface, respectively, cooperating to pinch the linear body therebetween.

Preferably, the drive device for a linear body is provided with a guide portion positioning the linear body when the linear body and the member to be secured are integrally attached to the securing portion.

Preferably, the securing portion has an elastic portion, and the member to be secured is sandwiched by the elastic portion and thus attached to the securing portion.

Preferably, the linear body is a linear body for medical use. Preferably, the linear body is any of a catheter, a guide wire and a delivery wire having a tip with an embolizing coil attached thereto.

Effects of the Invention

The present drive device for a linear body allows a portion to be secured and the linear body in a blood vessel, an aneurysm or the like to be manually removed from the drive device without substantially changing the position of the linear body when power failure or a similar emergency arises. This facilitates resuming a surgery manually.

DESCRIPTION OF THE REFERENCE SIGNS

1: drive device, 2: housing, 3: motor, 4: rotary shaft, 5: driving roller, 5a, 6a: rotation surface, 5b: feed groove, 6: driven roller, 7: supporting member, 8: elastic body, 10: lid member, 11: hinge, 12: lever, 13: projection, 14: engagement portion, 15: elastic portion, 16: small hole, 17: guide groove, 18: raised portion, 30: linear body, 31: Y connector.

BEST MODES FOR CARRYING OUT THE INVENTION

Hereinafter reference will be made to the drawings to describe the present invention in embodiments. In the figures, identical or corresponding components are identically denoted and will not be described repeatedly in detail.

First Embodiment

Figure 1:
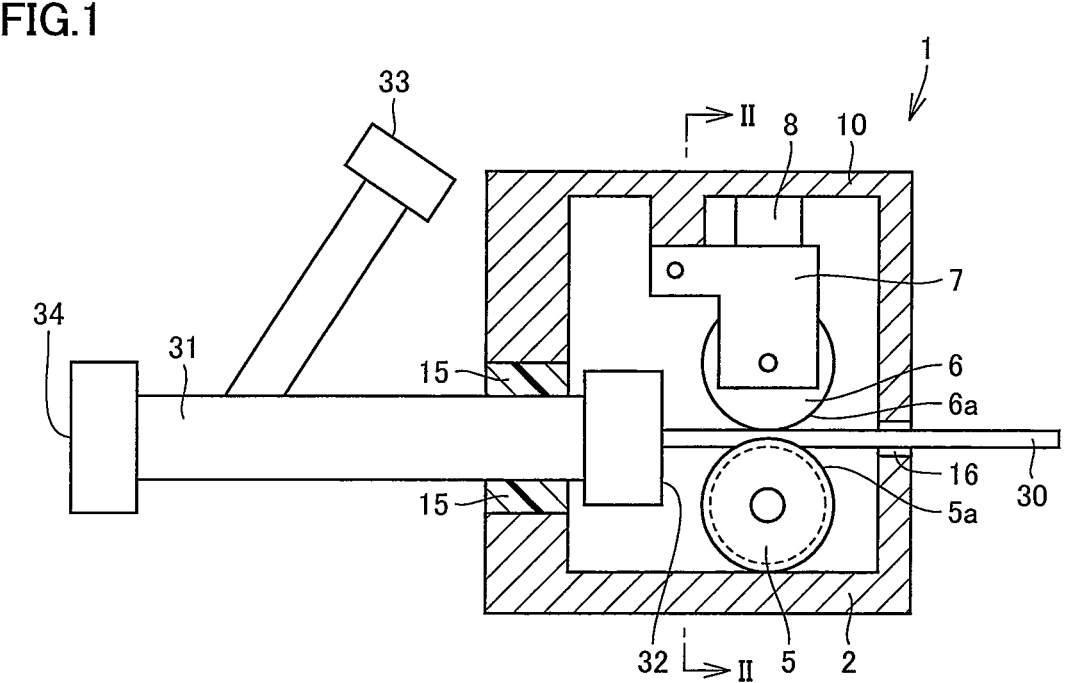
FIG. 1 is a schematic cross section of a drive device for a linear body in a first embodiment.
Figure 2:
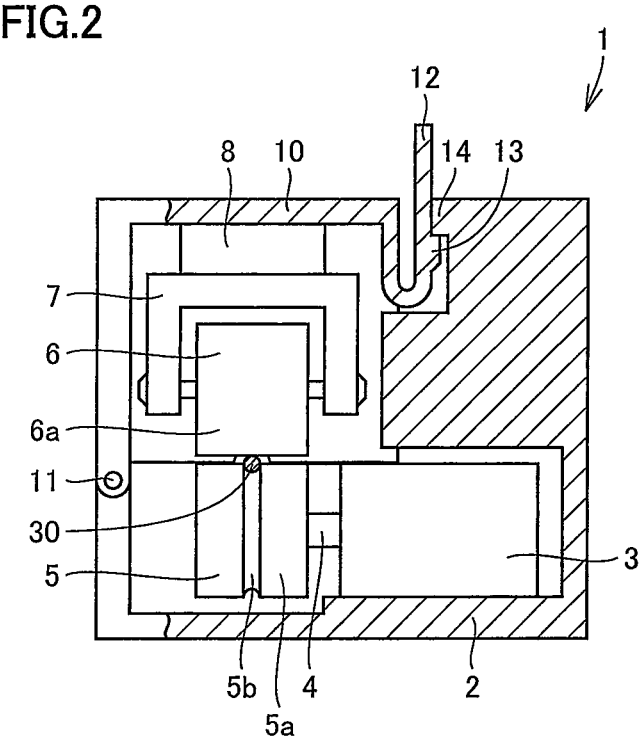
FIG. 2 is a partial schematic cross section of the drive device for the linear body, taken along a line II-II shown in FIG. 1.

FIG. 1 is a schematic cross section of a drive device for a linear body in a first embodiment. FIG. 2 is a partial schematic cross section of the drive device for the linear body, taken along a line II-II shown in FIG. 1. As shown in FIG. 1 and FIG. 2, a drive device 1 includes a housing 2. Housing 2 has a lid member 10 opened and closed, as desired, as it pivots around a hinge 11 serving as a spindle.

Housing 2 and lid member 10 define an internal space of drive device 1. In the internal space, a motor 3 serving as a torque generator, a rotary shaft 4 transmitting the torque generated by motor 3, and a driving roller 5 providing a rotational motion by the torque transmitted via rotary shaft 4 are provided. Driving roller 5, which is attached to motor 3 and serves as a feed roller, is generally cylindrical. Driving roller 5 has a cylindrical side surface, or a rotation surface 5a, having a feed groove 5b.

Disposed opposite to the driving roller 5 rotation surface 5a is a driven roller 6. Driven roller 6, which is a pressing roller applying pressure to a linear body 30, is generally cylindrical. Driven roller 6 has a cylindrical side surface, or a rotation surface 6a, which and the driving roller 5 rotation surface 5a cooperate to pinch linear body 30. The driving roller 5 rotation surface 5a and the driven roller 6 rotation surface 6a face each other with linear body 30 interposed. Linear body 30 is disposed between rotation surfaces 5a and 6a along feed groove 5b formed on driving roller 5 at rotation surface 5a.

When motor 3 is actuated and driving roller 5 accordingly provides rotational motion, driven roller 6 is driven by the rotation of driving roller 5 to provide rotational motion. Driving roller 5 and driven roller 6, rotating in opposite directions, respectively, move linear body 30 in its longitudinal direction. The linear body is driven by driving roller 5. Motor 3 generating torque, and driving roller 5 and driven roller 6 providing rotational motion are included in an actuator serving as a feed device moving linear body 30 in its longitudinal direction. The actuator pinches linear body 30 and moves it in its longitudinal direction.

The torque generator causing driving roller 5 to rotate is not limited to motor 3, and it may for example be an engine, a turbine or the like. Furthermore, it is not limited to the actuator moving linear body 30 by torque, and it may be any equipment that can convey elongate linear body 30 in a direction in which it extends.

It is desirable that the driving roller 5 rotation surface 5a and the driven roller 6 rotation surface 6a are formed such that when driven roller 6 is pressed against driving roller 5 to pinch linear body 30, linear body 30 can be moved smoothly and also protected from damage. For example, driving roller 5 and driven roller 6 can be formed of stainless steel and rotation surface 5a, 6a can be provided in the form of a coating of urethane resin or the like.

Driven roller 6 is provided in the internal space of drive device 1 and supported by lid member 10 with a supporting member 7 supporting driven roller 6 rotatably and an elastic body 8 posed therebetween. Driven roller 6 is supported such that it is suspended from lid member 10. Elastic body 8 is attached to lid member 10. Driven roller 6 is supported by lid member 10 with elastic body 8 for example of rubber posed therebetween.

Lid member 10 has a lever 12 operated to open and close lid member 10. Lever 12 is elastically formed. FIG. 2 shows lever 12 generally in the form of the letter U. Lever 12 is elastically deformable to decrease or increase the form of the letter U in width. Lever 12 has a projection 13. When projection 13 is engaged with housing 2 at an engagement portion 14, lever 12 is secured to housing 2.

Housing 2 and lid member 10 are provided with an elastic portion 15. As shown in FIG. 1, Y connector 31 is secured such that it is pinched by elastic portion 15 associated with housing 2 and elastic portion 15 associated with lid member 10. Y connector 31 has one through hole extending therethrough from a first input port 32 to reach an output port 34. Furthermore, Y connector 31 has another through hole extending therethrough from a second input port 33 to reach output port 34. Linear body 30 is inserted through one through hole of Y connector 31.

Y connector 31 is a member secured at a securing portion of drive device 1. The securing portion has a form of a hole formed at a portion at which a sidewall of housing 2 and a sidewall of lid member 10 are aligned, and elastic portion 15 of rubber or the like provided on an inner circumference of the form of the hole. Drive device 1 is capable of securing the member to be secured, or Y connector 31. The Y connector is sandwiched by elastic portion 15 attached to housing 2 and that attached to lid member 10, and is thus attached to the securing portion.

The sidewalls of housing 2 and lid member 10, respectively, that are provided with the securing portion capable of securing Y connector 31 are opposite to another side wall of housing 2 and another sidewall of lid member 10, and a small hole 16 is provided at a portion at which those other sidewalls are aligned. Small hole 16 is formed by partially cutting out the other side wall of housing 2 and that of lid member 10. Small hole 16 is formed to be slightly larger in diameter than linear body 30 to allow linear body 30 to be passed therethrough. Small hole 16 is formed substantially at a position where a virtual extension of a through hole of Y connector 31 intersects the other sidewalls of housing 2 and lid member 10 (typically, such that small hole 16 penetrates the other sidewalls in a direction matching that in which the through hole of Y connector 31 extends).

Drive device 1 has lid member 10 opened and closed in an operation, as will be described hereinafter. FIG. 1 and FIG. 2 show lid member 10 assuming a closed position. In this position, lever 12 is elastically deformed to reduce the form of the letter U in width to disengage projection 13 from engagement portion 14. Once projection 13 has been disengaged from engagement portion 14, lid member 10 is pivotable around hinge 11. In the FIG. 2 cross section, lid member 10 is pivoted around hinge 11 counterclockwise and thus opened. Lid member 10 has such a shape that lid member 10 can be opened manually by an operator holding and thus operating lever 12. Lever 12 can be elastically deformed to disengage projection 13 from engagement portion 14 to open lid member 10.

When lid member 10 is opened, elastic portion 15 attached to lid member 10 moves with lid member 10. Note that while lid member 10 is closed, elastic portion 15 exerts elastic force to hold Y connector 31. Once lid member 10 has been opened, this elastic force is no longer exerted to a portion of the outer circumference of Y connector 31. This allows Y connector 31 to be moved manually. Furthermore, driven roller 6 also moves with lid member 10. While the lid member 10 is closed, the driven roller 6 rotation surface 6a exerts force toward the driving roller 5 rotation surface 5a to press it. Once the lid member 10 has been opened, this force is relieved and linear body 30 having been pressed by the force is no longer pinched and can thus be moved manually. As lid member 10 is moved, small hole 16 has its perimeter partially opened, and linear body 30 can be moved not only in its longitudinal direction but also as desired.

As Y connector 31 and linear body 30 can both be moved manually, linear body 30 can be moved such that it is inserted in a through hole of Y connector 31, i.e., linear body 30 and Y connector 31 can be moved together. In other words, drive device 1 includes lid member 10 capable of opening a roller portion including driving roller 5 and driven roller 6, the securing portion securing Y connector 31, and small hole 16, and lid member 10 can be opened to allow linear body 30 and Y connector 31 to be together removed from the securing portion securing Y connector 31.

On the other hand, when lid member 10 assuming an open position is pivoted around hinge 11, lid member 10 moves in a direction allowing it to be closed. In the FIG. 2 cross section, lid member 10 is pivoted around hinge 11 clockwise and thus closed. Lid member 10 can be closed manually by an operator holding and thus operating lever 12. When projection 13 of lever 12 impinges on engagement portion 14, lever 12 is elastically deformed so that its U letter form is decreased in width. Projection 13 slides on a surface of engagement portion 14 and thus passes by engagement portion 14.

Once projection 13 has passed by engagement portion 14, lever 12 elastically deforms so that its U letter form increases in width, and projection 13 engages with engagement portion 14. When lid member 10 is pushed down toward housing 2 to come close thereto, the movement of driven roller 6 and supporting member 7 attached to lid member 10 toward housing 2 is prevented by driving roller 5 axially supported by motor 3 secured to housing 2. Accordingly, elastic body 8 sandwiched between lid member 10 and supporting member 7 is elastically deformed.

Elastic body 8 elastically deformed exerts elastic force as reaction, which presses lid member 10. The force exerted by elastic body 8 to lid member 10 causes projection 13 of lever 12 to closely contact engagement portion 14, and presses lever 12 against housing 2. Once lid member 10 has been closed, elastic body 8 presses lid member 10 with elastic force, which presses and thus fixes lever 12 against housing 2. Elastic body 8 exerts elastic force, which presses lever 12 against housing 2 and thus closes lid member 10.

When lid member 10 is open, Y connector 31 having linear body 30 through the through hole can be assembled to elastic portion 15 of housing 2. When lid member 10 is closed in this condition, Y connector 31 is sandwiched by elastic portion 15 associated with housing 2 and elastic portion 15 associated with lid member 10. Furthermore, linear body 30 is pinched by the driving roller 5 rotation surface 5a and the driven roller 6 rotation surface 6a and also positioned in small hole 16 so as to pass through small hole 16. Linear body 30 and Y connector 31 are supported in drive device 1 by elastic portion 15, between the roller portion's driving roller 5 and driven roller 6, and by small hole 16. Closing lid member 10 allows linear body 30 and Y connector 31 to be attached integrally to the securing portion of drive device 1.

Lid member 10 can be opened and closed manually by operating lever 12. As has been described previously, when lid member 10 is opened, linear body 30 and Y connector 31 can be integrally removed from the securing portion, and by closing lid member 10, linear body 30 and Y connector 31 can be integrally attached to the securing portion. In other words, according to the first embodiment, drive device 1 for linear body 30 allows linear body 30 and Y connector 31 to be integrally, detachably attached to the securing portion of drive device 1 manually.

As described above, drive device 1 that moves linear body 30 to deliver it in its longitudinal direction allows lid member 10 to be opened to allow linear body 30 inserted in Y connector 31 and Y connector 31 to be integrally removed from drive device 1 manually. If power failure or similar emergency arises and drive device 1 is stopped, linear body 30 and Y connector 31 can integrally be removed manually. As Y connector 31 connected to a catheter and linear body 30 can integrally be removed from drive device 1, the catheter and linear body 30 can have their positional relationship unchanged before and after they are removed. This allows a treatment to be immediately, manually resumed without substantially changing the position of linear body 30 in a blood vessel, an aneurysm or the like.

Second Embodiment

Figure 3:
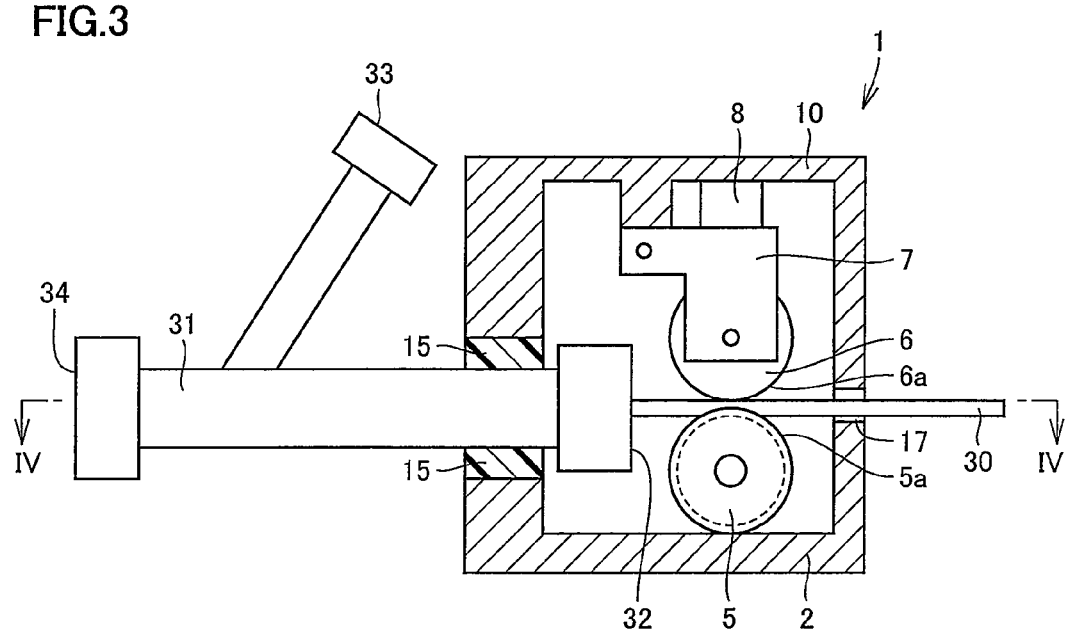
FIG. 3 is a schematic cross section of a drive device for a linear body in a second embodiment.
Figure 4:
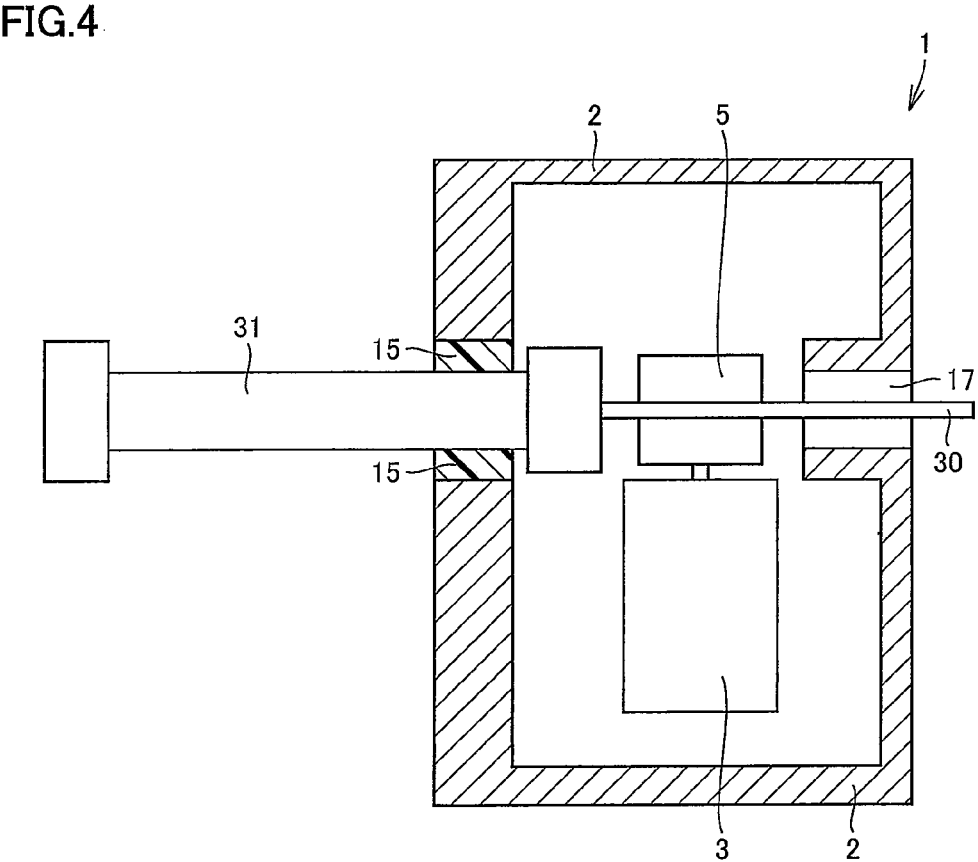
FIG. 4 is a partial schematic cross section of the drive device for the linear body, taken along a line IV-IV shown in FIG. 3.
Figure 5:
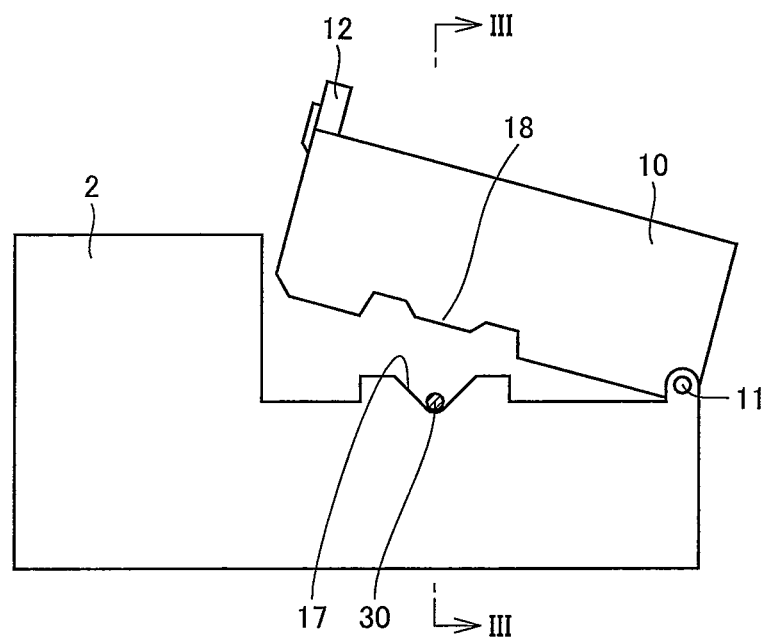
FIG. 5 is a side view of the drive device for the linear body in the second embodiment.
Figure 6:
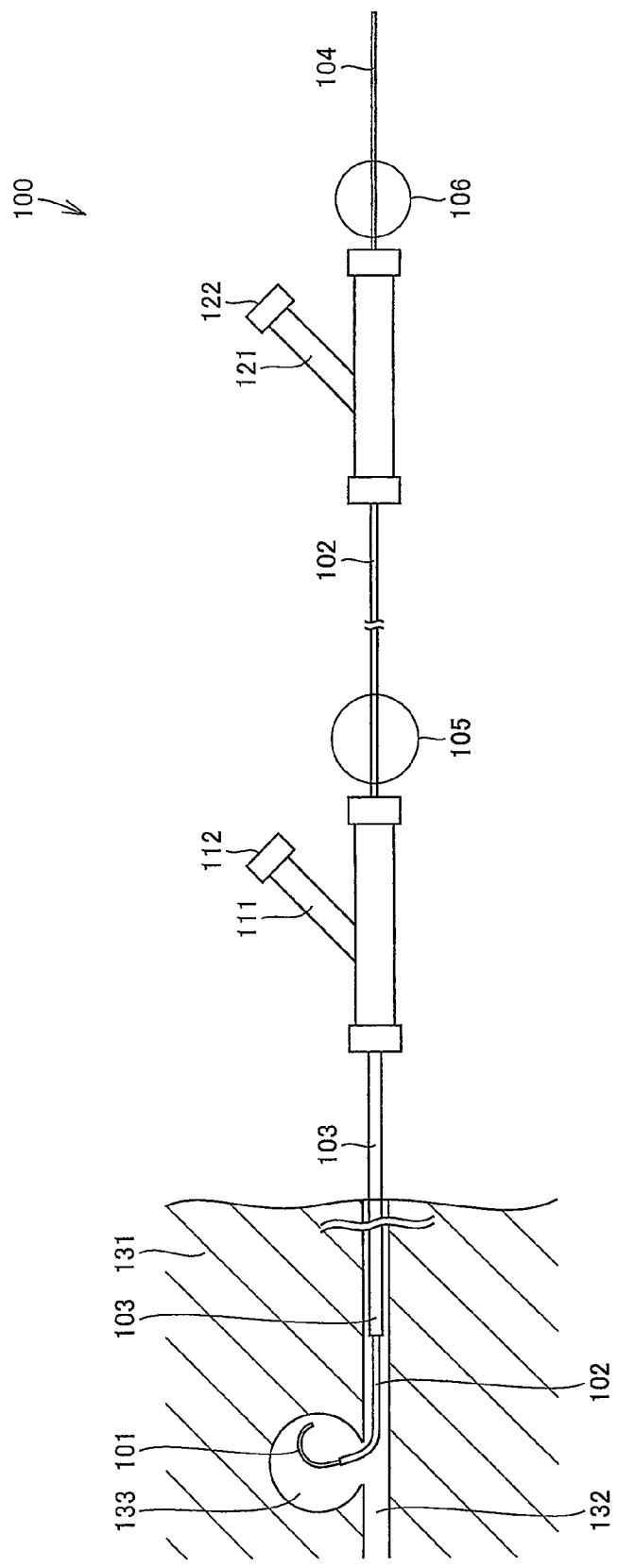
FIG. 6 schematically shows a medical instrument used in a treatment employing coil embolization.

FIG. 3 is a schematic cross section of a drive device for a linear body in a second embodiment, taken along a line shown in FIG. 5. FIG. 4 is a partial schematic cross section of the drive device for the linear body, taken along a line Iv-Iv shown in FIG. 3. FIG. 5 is a side view of the drive device for the linear body in the second embodiment. The second embodiment provides drive device 1 for linear body 30, that is different from the first embodiment in that the former has housing 2 and lid member 10 aligned at a portion shaped as shown in FIG. 3 to FIG. 5.

More specifically, elastic portion 15 is provided at one sidewall, and at the other sidewall opposite thereto, housing 2 has a portion aligned with lid member 10 and having a guide groove 17. Lid member 10 at the other sidewall has a raised portion 18 shaped to be fitted into guide groove 17. When lid member 10 is closed, raised portion 18 is fitted into guide groove 17, and raised portion 18 and guide groove 17 together define a space having a dimension slightly larger than the diameter of linear body 30.

In other words, when lid member 10 is closed to attach linear body 30 and Y connector 31 integrally to the securing portion of drive device 1, linear body 30 is positioned by guide groove 17. Drive device 1 is provided with guide groove 17 that serves as a guide portion for positioning linear body 30 and receives and passes linear body 30. Linear body 30 is placed in guide groove 17 at the deepest portion, which is formed substantially at a position where a virtual extension of a through hole of Y connector 31 intersects the other sidewalls of housing 2 and lid member 10 (typically, such that guide groove 17 has the deepest portion extending in a direction extending through the other sidewalls and matching a direction in which the Y connector 31 through hole extends).

When drive device 1 having the guide portion has lid member 10 closed, linear body 30 is positioned and set in position. Thus, when lid member 10 is closed, linear body 30 is set between driving roller 5 and driven roller 6 properly. Furthermore, such a disadvantage can be prevented/minimized that linear body 30 is pinched at a portion where lid member 10 and housing 2 are aligned, and is thus prevented from moving, damaged, and the like.

Guide groove 17 may be shaped in the from of the letter V, as shown in FIG. 5, or may be shaped in the form of the letter U, an arc, or a similar form having a curve having an appropriate radius of curvature.

As has been described in the first embodiment, linear body 30 and Y connector 31 can be attached to and detached from drive device 1 with linear body 30 inserted through a through hole of Y connector 31, i.e., integrally. However, it is not a requirement to attach linear body 30 and Y connector 31 integrally to drive device 1. More specifically, drive device 1 having a guide portion according to the second embodiment ensures that linear body 30 is positioned by the guide portion. As such, it is also possible that after lid member 10 is closed and Y connector 31 is attached to the securing portion, linear body 30 is inserted through the guide portion into drive device 1 and thus inserted through a through hole of Y connector 31. This can eliminate the necessity of constantly handling linear body 30 and Y connector 31 integrally, and thus enhance drive device 1 in operability.

Linear body 30 used for drive device 1 described in the first and second embodiments may be a linear body for medical use. For example, linear body 30 may be a flexible, linear medical instrument inserted into a blood vessel, a ureter, a bronchus, an alimentary canal, a lymphatic vessel, or other similar canals/ducts/tubes in a body, and guided to a target site by an operation performed outside the body. Typically, linear body 30 may be any of a guide wire, a catheter, and a delivery wire having attached at a tip thereof a coil used for embolizing an aneurysm.

It should be understood that the embodiments disclosed herein are illustrative and non-restrictive in every respect. The scope of the present invention is defined by the terms of the claims, rather than the description above, and is intended to include any modifications within the scope and meaning equivalent to the terms of the claims.

INDUSTRIAL APPLICABILITY

The present invention is advantageously applicable to drive devices used to insert coils used for treatments using the coils to embolize cerebral aneurysms, catheters used for guiding the coils to aneurysms or the like, and other similar linear medical instruments into canals/ducts/tubes in a body, in particular.

The invention claimed is:

1. A drive device for a linear body, comprising:
a securing portion configured to immovably secure a Y connector having a through hole in which a linear body is inserted; and
an actuator moving said linear body in a longitudinal direction of said linear body while said Y connector is stationarily held at said securing portion of said drive device, the drive device allowing said linear body and said Y connector to be integrally, manually attached to and detached from said securing portion, wherein:
said securing portion and said actuator are integrally formed in a housing of the drive device,
said securing portion has an elastic portion,
said Y connector is sandwiched by said elastic portion and thus attached to said securing portion; and
said linear body and said Y connector are integrally, manually removable from said drive device without substantially changing the position of said linear body within said Y connector in case of a power failure of said actuator, such that said linear body is configured to immediately, manually resume movement in said longitudinal direction.

2. The drive device for a linear body according to claim 1, wherein the housing comprises a lid member configured to open and close as desired, wherein by closing said lid member, said linear body and said Y connector are integrally attached to said securing portion, and by opening said lid member, said linear body and said member to be secured are integrally removable from said securing portion.

3. The drive device for a linear body according to claim 2, further comprising an elastic body attached to said lid member wherein:
said lid member has a lever operated to open/close said lid member
when said lid member is closed, said elastic body presses said lid member with elastic force, which presses and thus fixes said lever; and
said lever is elastically deformed to open said lid member.

4. The drive device for a linear body according to claim 1, wherein:
said actuator includes a torque generator, a driving roller performing rotational motion by torque generated by said torque generator, and a driven roller performing rotational motion as said driving roller rotates; and
said driving roller and said driven roller have a rotation surface and a rotation surface, respectively, cooperating to pinch said linear body therebetween.

5. The drive device for a linear body according to claim 1, provided with a guide portion positioning said linear body when said linear body and said Y connector are integrally attached to said securing portion.

6. The drive device for a linear body according to claim 1, wherein said linear body is any of a catheter, a guide wire and a delivery wire having a tip with an embolizing coil attached thereto.

* * * * *